United States Patent
Zhang

(10) Patent No.: US 7,306,669 B1
(45) Date of Patent: Dec. 11, 2007

(54) **PROCESS FOR ISOLATING A NATURAL RED PIGMENT FROM A SPECIES OF MICROALGAE, *TETRASELMIS* SP. MACC/P66**

(76) Inventor: Yushi Zhang, 11310 SE. 86 Pl., Newcastle, WA (US) 98056

(*) Notice: Subject to any disclaimer, the term of this patent is extended or adjusted under 35 U.S.C. 154(b) by 0 days.

(21) Appl. No.: 11/621,661

(22) Filed: Jan. 10, 2007

(51) Int. Cl.
- C09B 67/20 (2006.01)
- C09B 67/54 (2006.01)
- C09B 67/00 (2006.01)
- C09B 61/00 (2006.01)

(52) U.S. Cl. .................. 106/493; 106/499; 424/195.17

(58) Field of Classification Search .............. 106/493, 106/499; 424/195.17
See application file for complete search history.

(56) References Cited

FOREIGN PATENT DOCUMENTS

FR         2858771 A    *    2/2005

OTHER PUBLICATIONS

Chemical Abstract No. 57:31927, abstract of an article by Parsons entitled: "Pigment Composition of Eleven Species of Marine Phytoplankters", Journal of the Fisheries Research Board of Canada (1961), 18, 1017-25, no month.*

Chemical Abstract No. 122:182051, abstract of an article by Goes et al entitled: "Effect of UV-B radiation on the Fatty Acid Composition of the Marine Phytoplankton *Tetraslemis* sp.; Relationship to Cellular Pigments", Marine Ecology: Progress Series (1994), 114(3), 259-74, no month.*

Chemical Abstract No. 127:173393, abstract of an article by Wright et al entitled: "Evaluation of Methods and Solvents For Pigment Extraction", Monographs on Oceanographic Methodology (1997), 10 (Phytoplankton Pigments in Oceanography: Guidelines to Modern Methods, 261-282, no month.*

Chemical Abstract No. 137:277913, abstract of an article by Liu et al entitled: "Differences between Autotropic, Heterotropic and Mixotropic Growth of *Tetraselmis* sp.", Qingdao Haiyang Daxue Xuebao (2002) 32(4), 579-584, no month.*

* cited by examiner

*Primary Examiner*—Anthony J. Green

(57) ABSTRACT

A species of marine microalgae (*Tetraselmis* sp. MACC/P66) was found to secrete an unknown red pigment to the culture medium when itself was still keeping healthy.

The unknown red pigment was collected and purified from the culture medium by column chromatography using cation-exchange resins. A process for concentrating and isolating the red water soluble pigment from the culture medium of *Tetraselmis* sp. MACC/P66 was described in the present invention.

1 Claim, No Drawings

PROCESS FOR ISOLATING A NATURAL RED PIGMENT FROM A SPECIES OF MICROALGAE, *TETRASELMIS* SP. MACC/P66

FIELD OF THE INVENTION

The present invention relates to natural pigments. In particular, the invention relates to a natural red water soluble pigment isolated from the culture medium of a species of microalgae, *Tetraselmis* sp. MACC/P66.

BACKGROUND OF THE INVENTION

Colorants are either natural pigments or synthetic dyes. The commercial colorants must meet high governmental regulatory standards. Most of artificial colorants are toxic to human beings. In recent years, some federal approved artificial colorants have been reported to be toxic as food additives. The safety concern of artificial colorants arises interest in finding new natural pigments.

Currently, the market of natural pigments grows at a two-fold speed than that of synthetic dyes in the world. The huge market of color additives and color cosmetics has also prompted extensive research in finding more natural pigments from plants, insects and animals.

However, despite the huge efforts of the researchers, to date, the natural pigments available in industry are rare, particularly, the red water soluble pigment.

The object of the present invention is to isolate and purify an unknown natural pigment from the culture medium of a species of microalgae, *Tetraselmis* sp. MACC/P66.

DISCLOSURE OF THE INVENTION

The present invention is particularly described with respect to a newly found natural red water soluble pigment secreted from a species of microalgae, *Tetraselmis* sp. MACC/P66. The isolation process of this red water soluble pigment has also been described in details.

1. Culture of *Tetraselmis* sp. MACC/P66

*Tetraselmis* sp. MACC/P66 is a species of *Tetraselmis* isolated from the coast water of QingDao, China. MACC/P66 is morphologically similar to other species of *Tetraselmis*. *Tetraselmis* sp. MACC/P66 is characterized by secreting red water soluble pigment into the cultured medium, whereas itself is still keeping healthy during and after release of the red pigment into the culture medium.

2. Collection and Isolation of the Red Water Soluble Pigment

The initial step in collection of the red water soluble pigment is separation of the red pigment-containing medium from the microalgae through centrifugation.

The second step involves the preparation of the cation-exchange absorbent resins for column chromatography. The cation-exchange resins are pre-treated with strong alkali at room temperature, then saturated with cations.

The red pigment is absorbed using the cation-exchange resins, eluted from the column and the fraction is collected and dried to powder using vacuum freeze-drying method.

The invention is further illustrated in the following non-limiting examples.

EXAMPLES

I. Culture of *Tetraselmis* sp. MACC/P66

The culture medium becomes notable red when *Tetraselmis* sp. MACC/P66 is cultured under 5000 lux of light at 30° C. for a certain length of time.

II. Collection and Isolation of the Red Water Soluble Pigment

A. Separate the red pigment-containing medium from the microalgae through centrifugation at 3000 rpm.

B. Prepare the cation-exchange absorbent resins for column chromatography. First, weigh 500 g D401 cation-exchange resins, treated with 1000 ml of 40% NaOH at 20° C. for 20 h. Wash out NaOH from the cation-exchange resins completely by distilled water. Second, saturate the cation-exchange resins with 1000 ml of 20% $MnSO_4$ for 2 h under electromagnet agitation. Wash out $Mn^{+2}$ from the cation-exchange resins completely by distilled water. Finally, add D401 cation-exchange resins to a 70 cm×4.0 cm column.

C. Add red pigment-containing medium to the top of the column at a speed of 1 liter/h at the bottom exit until all of the absorbent resins becomes red. Wash the absorbent resins with distilled water until no detection of $Cl^-$. Elute the column with 0.5 N ammonia and collect the 600-2000 ml fraction. The fraction is then collected and dried to powder using vacuum freeze-drying method.

I claim:

1. A process for the concentration and isolation of a red pigment from a culture medium of *Tetraselmis* sp. MACC/P66, the process comprising the steps of:
   a) Culturing *Tetraselmis* sp. MACC/P66;
   b) Separating a red pigment-containing medium from said *Tetraselmis* sp. through centrifugation;
   c) Collecting and concentrating the red pigment utilizing cation-exchange column chromatography.

* * * * *